United States Patent [19]
Torgalkar et al.

[11] Patent Number: 5,250,042
[45] Date of Patent: Oct. 5, 1993

[54] OSTOMY BAG WITH FILTER COMBINATION

[75] Inventors: Anil M. Torgalkar, E. Windsor; Frank S. Castellana, Princeton, both of N.J.

[73] Assignee: E. R. Squibb & Sons, Inc., Princeton, N.J.

[21] Appl. No.: 482,138

[22] Filed: Feb. 20, 1990

[51] Int. Cl.$^5$ .............................................. A61F 5/44
[52] U.S. Cl. .................................... 604/333; 604/339
[58] Field of Search ............... 604/332, 333, 335, 337, 604/338, 339, 126

[56] References Cited

U.S. PATENT DOCUMENTS

| | | | |
|---|---|---|---|
| 3,778,971 | 12/1973 | Granger et al. | 604/126 X |
| 4,372,308 | 2/1983 | Steer et al. | 604/333 |
| 4,387,712 | 6/1983 | Briggs et al. | 604/333 |
| 4,460,392 | 7/1984 | Poulsen et al. | 604/333 |
| 4,668,258 | 5/1987 | Steer | 604/333 X |
| 4,723,951 | 2/1988 | Steer | 604/333 |
| 4,940,461 | 7/1990 | Steer | 604/333 |

FOREIGN PATENT DOCUMENTS

| | | | |
|---|---|---|---|
| 2149306 | 6/1985 | United Kingdom | 604/333 |
| 2177301 | 1/1987 | United Kingdom | 604/333 |

Primary Examiner—Randall L. Green
Assistant Examiner—Elizabeth M. Burke
Attorney, Agent, or Firm—Stuart E. Krieger

[57] ABSTRACT

An ostomy bag having a stomal aperture to receive a stoma in one wall of the bag and a gas venting aperture in the bag with a filter element covering the gas venting aperture, the bag including an intervening membrane disposed between the front rear walls of the bag and between the stomal aperture and the gas venting aperture. The intervening membrane is liquid impermeable and gas permeable and supports an adequate flow rate of gas for ostomy bag applications. The intervening membrane preferably comprises a polytetrafloroethylene, microporous semi-permeable membrane laminated to a thermoplastic film layer which is heat sealable to the walls of the bag.

7 Claims, 4 Drawing Sheets

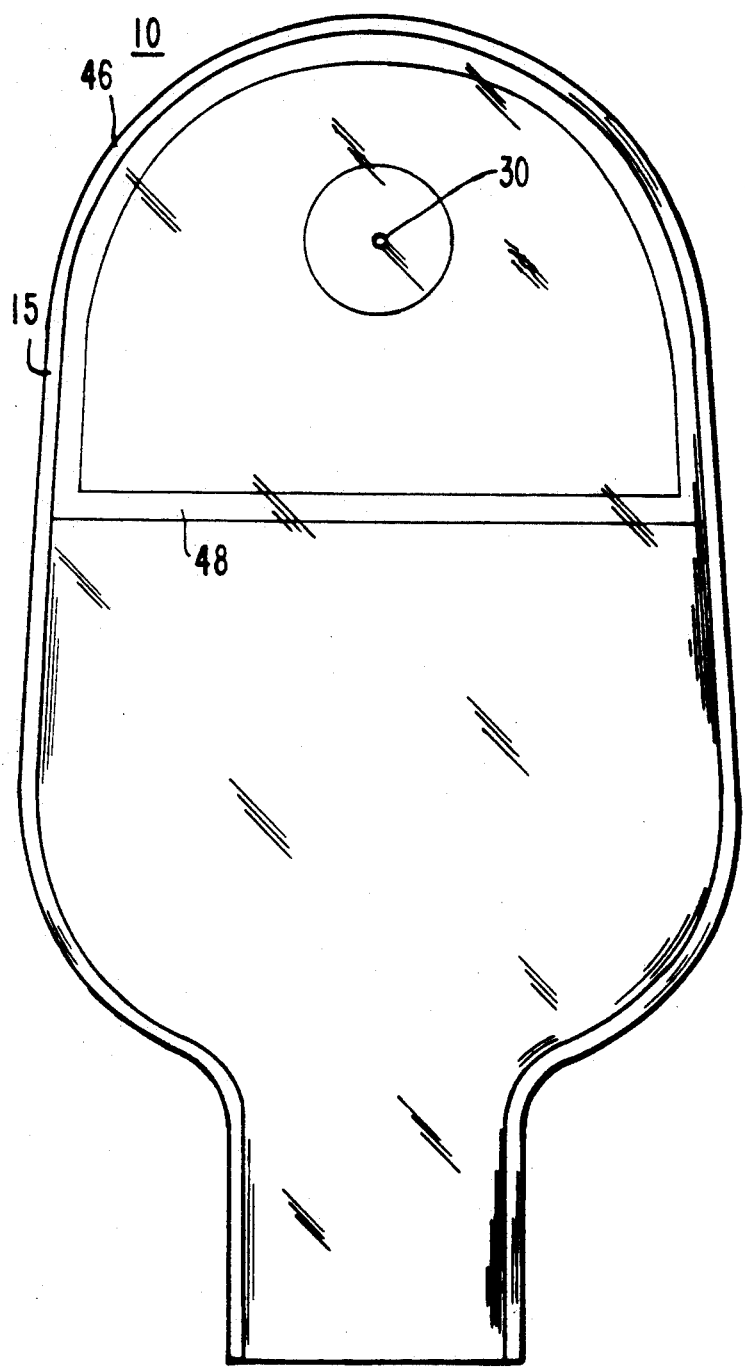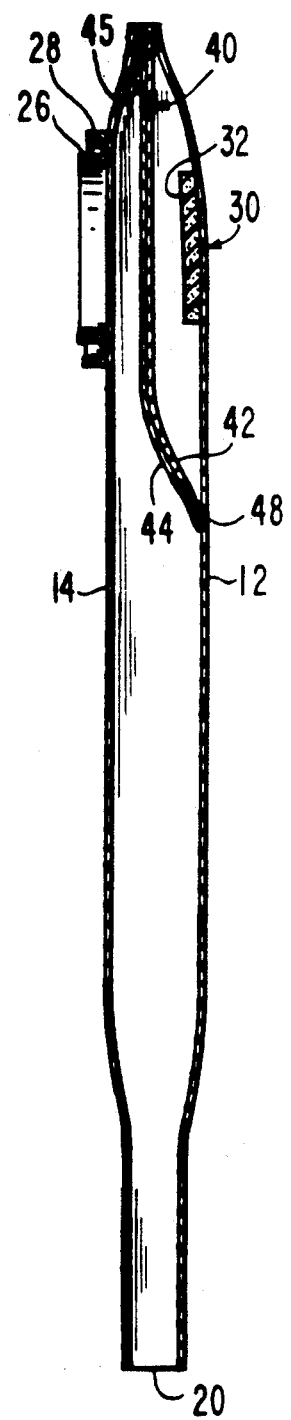

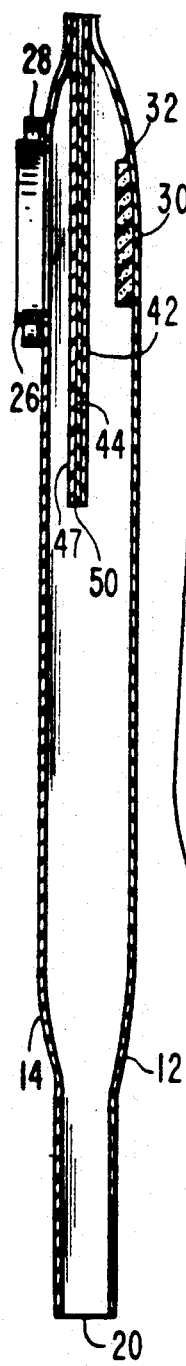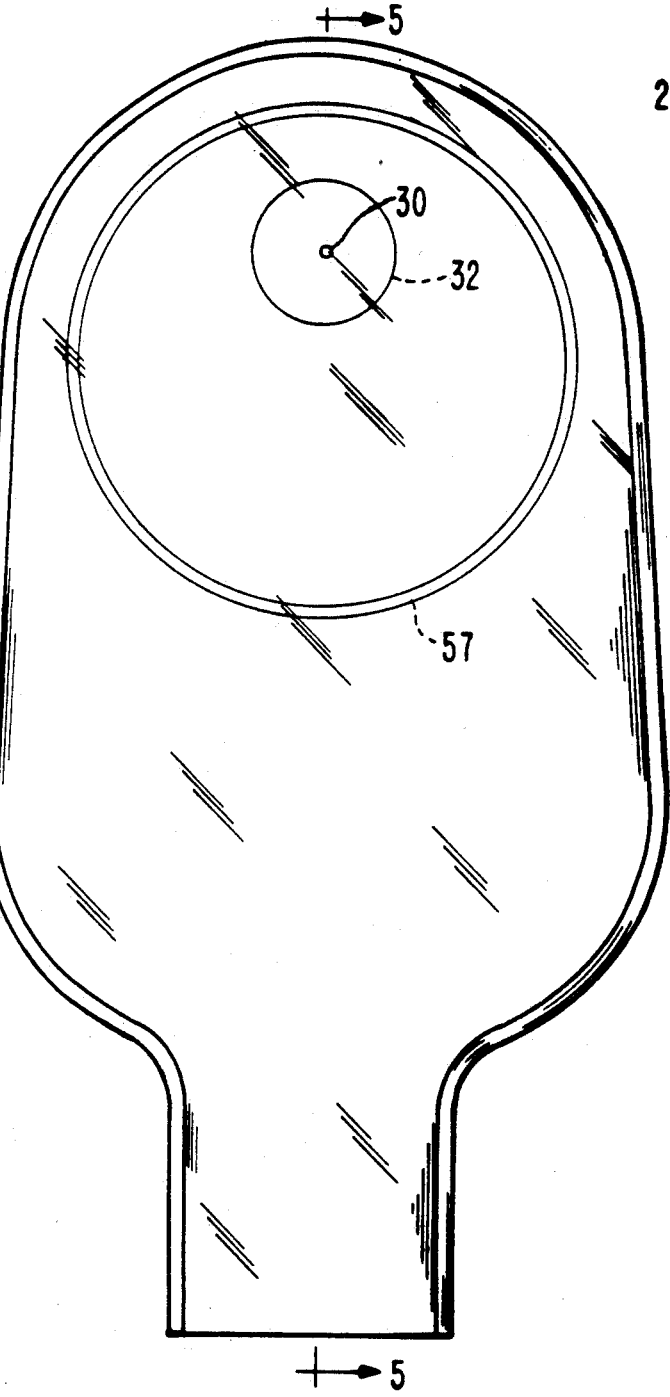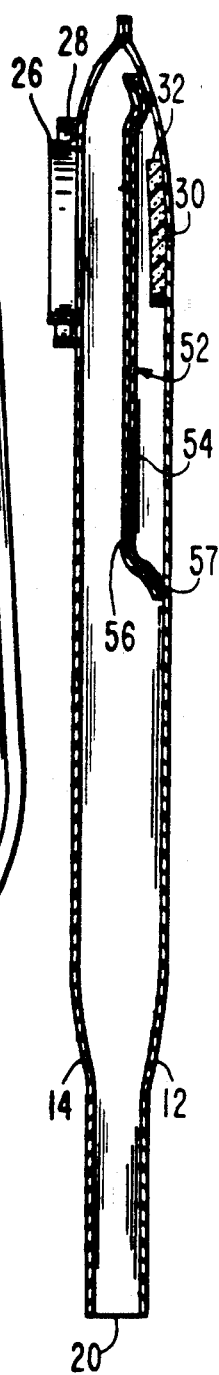

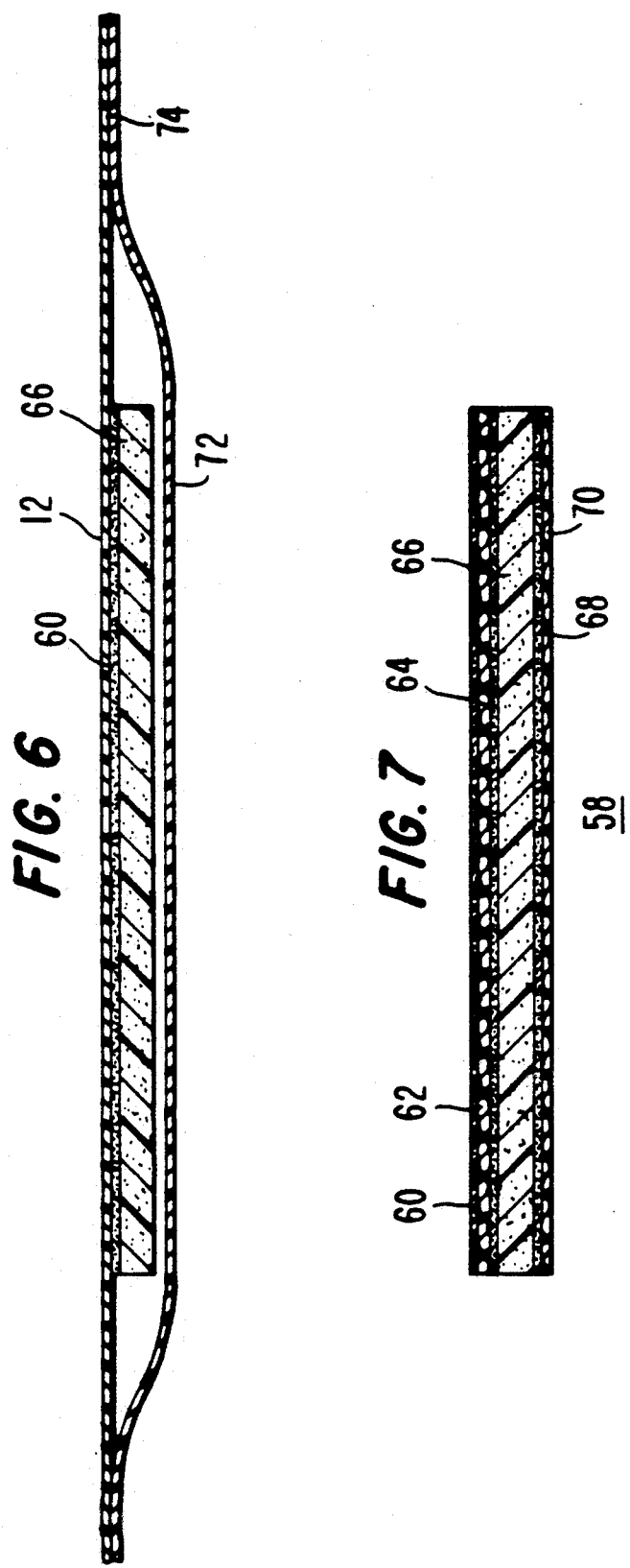

OSTOMY BAG WITH FILTER COMBINATION

BACKGROUND OF THE INVENTION

This invention relates generally to ostomy bags, and more particularly to ostomy bags with filters. Ostomy bags are usually secured to a pad or surgical dressing which contacts the user's skin and surrounds the stoma. Some patients have a problem with emission of flatus gases and it has been proposed to approach this problem by providing colostomy bags with carbon filters secured to one face of the bag over and around a gas outlet aperture from the bag. The gas is then escaped through this filter and the odors are reduced.

The problems are particularly acute, firstly from the point of view of the positioning and effectiveness of the filter, secondly from the point of view of ease of manufacture of the bag, and thirdly from the point of view of ease, comfort and unobtrusiveness in wear, when the user is unfortunate to have suffered an ileostomy operation with the result that discharge usually has the form of a relatively liquid slurry. In consequence, choking of the filter is all too common. Filter clogging is even more serious with drainable bags which are intended for longer term use than closed end non-drainable bags.

SUMMARY OF THE INVENTION

According to the invention, there is provided an ostomy bag having front and rear walls of a thermoplastic film with the rear wall having a stoma aperture. A filter is attached to one of the walls over an opening in the wall through which gases exit the bag. An intervening membrane is located between the front and rear walls of the bag and is disposed between the stomal opening and the filter. The intervening membrane is heat sealable to the walls of the bag, and is microporous allowing gas to flow through the membrane at a substantial rate but being liquid impermeable. The pore size of the membrane may range from 0.1 micron to 6 or more microns but is preferably between 0.2 and 0.5 microns. In one embodiment, the membrane comprises a liquid impermeable, gas permeable layer which, in the preferred embodiment, comprises a fibrillated polytetrafloroethylene semipermeable membrane. Other gas porous membranes may be created using interpenetrating network technology. Also, the intervening membrane in the preferred embodiment comprises a thermoplastic film layer attached to at least one surface of the liquid impermeable, gas permeable layer. Suitable materials for the thermoplastic film are polyethylene, polyester or a number of the polyolefins.

The intervening membrane is relatively large compared to the area of the filter surface, maybe as much as five times as large or more. The intervening membrane may be attached around the periphery of the opening covered by the filter to the interior surface of the wall to which the filter is attached, or the intervening membrane may be attached to both the front and rear walls of the bag along the top and side peripheries of the bag.

With the arrangement just described flatus gases, but not the liquid-solid discharge, can pass through the intervening membrane with the gases being vented through the filter but the filter does not become clogged with the liquid-solid discharge.

It is necessary in designing a filter arrangement such as the one described herein, that there be adequate air flow through the liquid impermeable, gas permeable layer, otherwise, the bag will tend to develop elevated gas pressure and form an unsightly or uncomfortable bulge in the bag. This is unacceptable. While it is mentioned in some prior art references that a filter arrangement could be designed to be liquid impermeable and gas permeable, none that the inventor is aware of have been disclosed in such detail as to teach one how to make an acceptable filter membrane that would provide an adequate rate of gas flow while still maintaining an almost absolute impermeability to liquid discharge. In the intervening membrane described herein, a gas flow of 100 cubic centimeters (cc) per centimeter squared at at least 6 centimeters of water pressure in one minute is obtainable. This relatively large rate of air flow, while maintaining the liquid impermeability of the barrier, is not to the inventor's knowledge shown anywhere in the prior ostomy art.

BRIEF DESCRIPTION OF THE DRAWINGS

The invention will be better understood from the following non-limiting particular description of embodiments thereof given with reference to the accompanying drawings in which:

FIG. 2 is a front view of the bag of FIG. 1;

FIG. 3A is a cross-section through the center of the bag on the lines and arrows 3A—3A in FIG. 1;

FIG. 3B is an alternate embodiment of the cross-section of FIG. 3A;

FIG. 4 is an alternate embodiment of the front view of a bottom emptying ileostomy bag according to an alternate embodiment of the invention;

FIG. 5 is a cross-section of the bag of FIG. 4 along the lines and arrows 5—5;

FIG. 6 is a cross-section through part of the wall of the ostomy bag containing a filter;

FIG. 7 is an enlarged cross-sectional view of the filter portion of FIG. 6 showing its laminated construction.

DETAILED DESCRIPTION OF THE DRAWINGS

Figure 1:
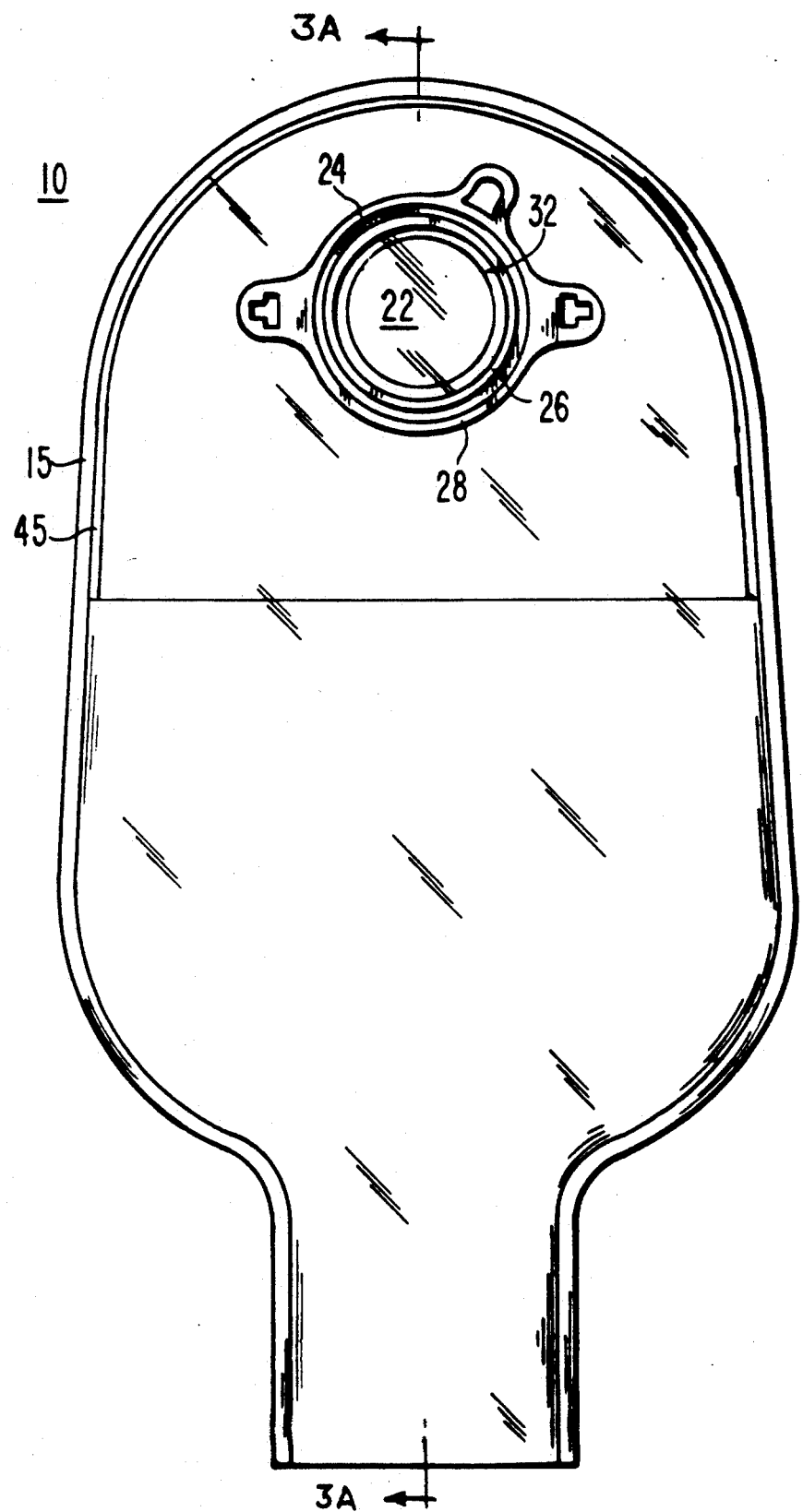
FIG. 1 is a rear view of a bottom emptying ileosotomy bag according to an embodiment of the invention.

Referring to the drawings, a drainable collection bag designated generally 10 comprises front and rear walls 12 and 14, respectively, formed of a suitable synthetic plastics material. The walls are welded together by a weld seam 15 around substantially the whole of their periphery. The lower end of the bag narrows and ends in an opening 20 which allows discharge of the material collected in the bag.

A material suitable for use as the walls of the bag should be gas and liquid impermeable. One such material comprises a trilaminate of polyethylene vinyl acetate (EVA) copolymer on the inner and outer laminates with a center layer of polyvinylidene chloride (PVDC) material. For the sake of simplicity in the cross-sectional views of FIGS. 3A, 3B and 5, the walls of the bag are shown as a single layer. The trilaminate is commercially available from W. R. Grace Co.

The rear wall of the bag comprises a stoma aperture 22 adapted to receive the stoma of a patient. The bag further comprises a first coupling member 24 which is secured by heat welding to the rear wall of the bag around the stoma aperture 22. The coupling itself defines a stoma aperture which aligns with the aperture 22 in the bag. The stoma aperture, of course, need not be circular but could be of any suitable shape.

The first coupling member 24 is of channel shape seen in any radial cross-section, such as, in FIG. 3A, and has a radially inner wall 26 and a radially outer wall 28. A second coupling member (not shown) is also circular in shape and defines an aperture to receive the stoma of the patient. The second coupling member is made of two parts, preferably integral with each other, namely a flange and a circular rib or projection which cooperates with the channel shaped first coupling member 24. The flange has a circular aperture and is intended to be secured to a pad or a surgical dressing which has a similar circular aperture and whose opposite surface contacts the skin of the patient. Details of the coupling members are described in U.S. Pat. No. 4,460,363 which is hereby incorporated by reference as if specifically set forth herein.

The front wall of the bag comprises a small gas venting aperture 30 which allows the interior of the bag to be in communication with ambient atmosphere. A circular filter 32 is attached to the wall of the bag and covers the gas venting aperture 30. The filter 32 in the Figures is shown attached to the interior of the front wall of the bag 10 over the gas venting aperture 30. The filter 32 is attached with a layer of adhesive or some suitable means to affix the filter to the bag wall, the filter 32 being preferably a carbon impregnated crushed polyurethane open cell foam or equivalent.

The bag further comprises an intervening membrane designated generally 40 which is located between the front and rear walls of the bag in the interior of the bag and is disposed between the stomal aperture 22 and the filter 32 and the gas venting aperture 30. The intervening membrane comprises two layers laminated together comprising a thermoplastic polymer film layer 42 which is heat sealable to the walls of the bag, and a liquid impermeable, gas permeable layer 44 which is laminated to the thermoplastic polymer film layer. A suitable thermoplastic film layer comprises polyethylene or a polyester or other heat sealable thermoplastic polymers such as those taken from the class of polyolefins. The thermoplastic film layer itself must be gas permeable. Thermoplastic film layers which are themselves gas permeable to the extent required for ostomy filter applications, are also liquid permeable.

While the thermoplastic film layer must be heat sealable to the bag wall(s) and gas permeable, the other layer must be highly liquid impermeable, but gas permeable, allowing a sufficiently high rate of gas flow therethrough which will be acceptable to ostomates and not cause the bag to collect gas and bulge. A suitable layer can be formed from fibrillated polytetrafluoroethylene (PTFE) in the form of a polytetrafluoroethylene semipermeable membrane. This material is available as Macroporous PTFE from Tetratec Corporation of Feasterville, Pa. See U.S. Pat. No. 3,953,566 which describes how to make tetrafluoroethylene polymers of high porosity. Suitable gas permeable liquid impermeable layers with adequate gas flow rates can be made using interpenetrating network technology.

In FIGS. 2 and 3A the intervening membrane 40 is shown heat sealed by weld 46 to the periphery of the bag at its top and along its sides. Because the layer 44 is not heat sealed to the bag walls, a perimeter strip of thermoplastic polymer material 45, the same as layer 42, is laminated to the periphery of layer 44 where it is to be heat sealed to the bag. Of course, a complete layer 47 of thermoplastic polymer could be heat sealed on both sides of the layer 44 when layer 44 is to be attached along its upper and side peripheries to the bag walls. See, for example, FIG. 3B. Intervening membrane 40 is heat sealed along its bottom to the front wall 12 of the bag along the weld line 48. The intervening membrane thus encloses the filter 32 and separates it from the stoma aperture 22 in a region in the upper part of the bag 14. In the embodiment shown in FIG. 3A, the filter 32 and gas venting aperture 30 are directly across from the stoma aperture. Because the intervening membrane 40 is liquid impermeable, but gas permeable, it will allow gas to pass through into the chamber surrounding the filter and then through the filter and out of the bag through the aperture 30, but it will not allow liquid or solid waste to pass through and thereby clog the filter 32. In FIG. 3B, the intervening membrane 40 is shown unattached to either of the bag walls along its bottom edge 50 but the membrane 40 is still located intermediate the stoma aperture 22 and the filter 32.

FIGS. 4 and 5 show a third alternate embodiment wherein the intervening membrane 52 is generally circular in shape with a liquid and gas permeable thermoplastic polymer layer 54 and a liquid impermeable, gas permeable layer 56. The membrane is heat sealed to the front wall of the bag only around the filter 32 along circular weld 57. In this embodiment the intervening membrane is not sealed to the periphery of the bag. This necessitates only that the thermoplastic film 54 be laminated to just one side of the layer 56.

FIGS. 6 and 7 show one embodiment for a filter assembly to be used with the intervening membrane 40. Referring first to FIG. 7, a preferred filter assembly 58 comprises a layer of hot melt adhesive 60 whereby the filter may be affixed to the wall of the bag; a layer of microfine woven material 62; a matrix layer of hot melted adhesive 64; a filter disk of carbon impregnated crushed polyurtheane open cell foam 66 like the disc 32; a matrix layer of hot melt adhesive 68; and a layer of non-woven fabric 70.

In addition to the intervening member 40, a separate intervening wall 72 made of ethylene butylacrylate which is a synthetic plastics material may be included. This is shown not connected to the filter assembly 58, but connected to the bag wall by a closed loop weld 74 entirely surrounding the filter assembly 58. The synthetic plastics material will be needled at about 160 holes per square inch or between 100 and 300 holes per square inch. The holes are preferably substantially circular with a maximum dimension of each hole from 75 to 300 microns. This provides additional protection against liquid penetration but still allows adequate gas flow.

At least five different successful intervening membrane configurations were assembled and the air flow and water permeability tested. Each of the configurations had an overall laminate thickness of 3 mils and had excellent flexibility, a critical requirement for use in ostomy bags. Flexibility was measured by hand manipulation. Each configuration was subjected to two water and two airflow permeability tests. The two water tests were a beaker test and a pouch test. In the beaker test, approximately 150 cubic centimeters (cc) of water was poured in a beaker and then the membrane was tightly placed on top of the beaker. The beaker was then turned upside down and water permeability through the film was observed for five minutes. In the pouch test, a pouch was prepared with a membrane configuration as one wall of the pouch. The pouch was then filled with water and placed on a bench top with the membrane side of the pouch at the bottom. Water absorbing nonwoven paper was placed on the bench top to observe water leakage through the membrane.

The air permeability was measured using two tests. The first follows the ASTM method D-726-58, method A, and TAPPI Standard T460M49, using a Gurley densometer, model 4110. The second test is an in-house pouch leak detecting test method. In the in-house test, the pouch was prepared with one side of the pouch made of usual pouch film and the other side made from the intervening membrane configuration. A flange on the pouch was attached to a pouch leak detection apparatus and the pouch was filled with approximately 400 cc of air until a water manometer indicated 60 mm of pressure. The air pressure inside the pouch was measured throughout the test by a water manometer. The pouch was then placed on a bench top and about 100 grams ring weight was placed on the pouch. The ring weight is used to distribute the weight over a larger pouch surface. A stop watch was started at the same time. The time required for deflation of the pouch was determined and the experiment was discontinued when the pressure differential between the inside of the pouch and the ambient atmosphere reached 5.0 mm of water.

A 4-6 CFM PTFE film commercially available from Tetratec using a Reemay 2250 polyester film thermobonded to the PTFE film and a laminate thickness of 3 mils was tested. The PTFE film had a pore size of less than 1.0 micron. The term "CFM" refers to air flow through the film in cubic feet per minute per square foot as measured by the ASTM Method F778-82. No water leaked through the membrane in either of the water permeability tests. The air flow of 300 cc through the intervening membrane using the Gurley method took less than 1.6 seconds, while venting of the air in the pouch using the in-house test took less than 15 minutes. In a second configuration, a 10-12 CFM Tetratec PTFE film with Reemay 2250 polyester thermobonded to the PTFE film was tested. This configuration had a limiting pore size of 1.6 microns. Again no water leakage was measured and the air flow of 300 cc was less than 0.9 seconds, while the in-house method took less than 10 minutes. In a third configuration, a 1.5 mil thick Tetratec PTFE film of 0.45 micron pore size was thermobonded to a non-woven fabric made from high density polyethylene or polypropylene through a process of extrusion, embossing and orientation. Frazier Air Permeability of the high density polyethylene non-woven fabric ranged between 1000 to 1200 cubic feet/per minute/per square foot. The high density polyethylene fabric, which is thermobonded to Tetratec PTFE film, is commercially produced by Applied Extrusion Technologies, Inc. of Middletown, Del. under the brand name DELNET non-woven fabrics. Theoretically, any thermoplastic of the polyolefin family with sufficient gas permeability could be used for thermobonding. Again, no water leakage was present and the air flow was less than 0.9 seconds using the Gurley method and less than 12 minutes with the in-house air permeability method. A Tetratec PTFE layer was thermobonded to a Reemay 2250 polyester film in a fifth configuration in which the pore size of the PTFE layer was 0.22 microns. Again, similar results were obtained as for the immediately above mentioned configuration. There was no water permeability, air flow took less than 0.9 seconds with the Gurley method and less than 20 minutes with the in-house method. Finally, a Tetratec PTFE layer with a pore size of 0.22 microns was thermobonded to a polyethylene layer. Similar results were obtained.

In a configuration using a 25 CFM PTFE film having an unknown pore size, the water permeability was unacceptable probably due to very large pore size. A Reemay 2301-1 polyester film thermobonded to a Tetratec PTFE layer with an unknown pore size was tested. The water permeability was acceptable but the air flow through the layer using the Gurley instrument method took 212 seconds.

In general, intervening membranes made from commercially available PFTE, microporous, semipermeable film thermobonded to commercially available gas permeable, polyethylene or polyester film provide for no water permeability and good air permeability.

As can be seen from the Figures, the area of the intervening membrane 40 is quite a bit larger than the area of the filter 32 enclosing the gas venting aperture 30. The area can be as much as 2-5 times larger than the area of the filter or even larger. Because the area is so large and because of the excellent air permeability of the intervening membrane, gas will flow readily through the intervening membrane and out the filter through the gas venting aperture. If liquid or solid discharge from the stoma does impinge on the intervening membrane it will not remain long because of the excellent surface tension characteristics of the membrane. If some blockage does occur, gas permeability will not be substantially affected because the intervening membrane is so large that the unblocked portion will support adequate gas flow. Because no liquid or solid passes through the intervening wall, there is no blockage of the filter element which has been a common and persistent problem in previous designs.

To give an example of the increased performance of this intervening membrane over material such as MICROPORE ™ microporous tape from 3M Company, which is somewhat gas porous but liquid impermeable, at 6-10 centimeters (cm) of water pressure the intervening membrane of this invention will support an air flow rate of at least 100 cc per cm$^2$ per minute. A MICROPORE-like material provides a rate less than 15 cc per cm$^2$ per minute at this pressure.

The intervening membrane of the present invention also prevents gas absorption filter from clogging by solid particles in the fecal matter, thus maintaining gas odor absorption efficiency of the filter.

What is claimed is:

1. A bag for receiving waste discharge from the human body comprising:
   front and rear walls formed of polymeric material, said walls having edges sealed together, said rear wall having a stomal aperture; a filter attached to one of the walls over a gas venting opening in the wall through which filtered gases exit the bag; and
   an intervening membrane located between the front and rear walls of the bag disposed between said stomal opening and said filter, said intervening membrane including a thermoplastic film sealable to said walls, said film being secured to at least one surface of a liquid impermeable, gas permeable sheet of microporous polytetrafluoroethylene having pore sizes from 1 to 6 microns, said intervening membrane having a gas flow rate of at least 100 cubic centimeters per centimeter squared per minute at at least 6 centimeters of water pressure.

2. The bag of claim 1 wherein said pore size is between 0.2 microns and 0.5 microns.

3. The bag of claim 1 wherein said heat sealable thermoplastic film layer comprises polyethylene.

4. The bag of claim 1 wherein said heat sealable thermoplastic film layer comprises polyester.

5. The bag of claim 1 wherein said intervening membrane is attached around the periphery of said opening associated with said filter to the interior surface of the wall to which said filter is attached.

6. The bag of claim 1 wherein said filter is attached to the interior surface of said front wall.

7. The bag of claim 1 wherein said intervening membrane is attached to both the front and rear walls of the bag around the top and side peripheries and along its bottom edge to the wall to which said filter is attached.

* * * * *